United States Patent [19]

Kiesele et al.

[11] Patent Number: 5,702,576
[45] Date of Patent: Dec. 30, 1997

[54] ELECTROCHEMICAL MEASURING CELL

[75] Inventors: Herbert Kiesele, Lübeck; Rigobert Chrzan, Bad Oldesloe; Frank Mett, Lübeck, all of Germany

[73] Assignee: Drägerwerk Aktiengesellschaft, Lübeck, Germany

[21] Appl. No.: 603,462

[22] Filed: Feb. 20, 1996

[30] Foreign Application Priority Data

Apr. 15, 1995 [DE] Germany ............... 195 14 214.4

[51] Int. Cl.⁶ ................................................. G01N 27/26
[52] U.S. Cl. ........................ 204/415; 204/431; 204/432
[58] Field of Search ........................... 204/415, 431, 204/432

[56] References Cited

U.S. PATENT DOCUMENTS 5,372,696  12/1994  Kiesele et al. ................ 204/415

FOREIGN PATENT DOCUMENTS 43 35 409 A1  4/1995  Germany.

Primary Examiner—Bruce F. Bell
Attorney, Agent, or Firm—McGlew and Tuttle

[57] ABSTRACT

The present invention pertains to an electronic measuring cell for detecting components in fluid media. Such a measuring cell is to be improved such that hermetic sealing of the contact wires leading out of the measuring cell is possible in a housing of a slightly modified design to prevent electrolyte from escaping. To achieve this, an annular space extending in parallel to the circumferential direction of the housing between the measuring cell cover and the housing is filled with an electrolyte- and temperature-resistant sealing material, and the contact wires are led through.

20 Claims, 1 Drawing Sheet

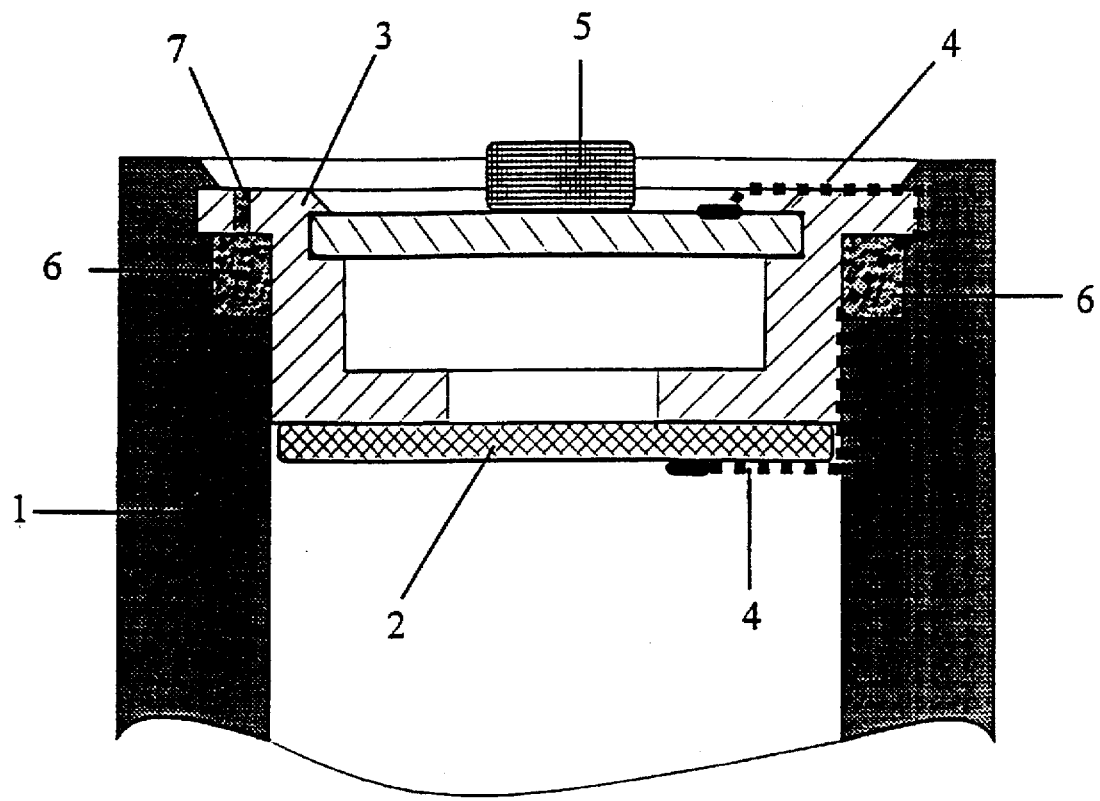

ELECTROCHEMICAL MEASURING CELL

FIELD OF THE INVENTION

The present invention pertains to an electrochemical measuring cell for detecting components in fluid media, which accommodates, within a housing, a measuring electrode and a counterelectrode each, both of which are in liquid connection with an electrolyte, and wherein one side of the housing has a gas-permeable, electrolyte-impermeable diaphragm, via which the components to be detected are brought into diffusion contact with the measuring electrode, and the other side of the housing is closed with a measuring cell cover.

BACKGROUND OF THE INVENTION

Such an electrochemical measuring cell is described in DE-4335409. One measuring electrode and one counterelectrode are located in the prior-art measuring cell. The contact wires of the measuring cell, which are usually lead between the housing wall and the measuring cell cover into the outer space of the measuring cell and are connected there to a conductor board with preamplifier, signal-processing unit and additional electronic components and, on the output side, to a connector for transmitting and evaluating the measuring signals, are arranged on the side of the housing, in the front opening of which the counterelectrode is located.

The counterelectrode and the measuring electrode are in liquid connection with a suitable electrolyte (electrolyte solution), which depends on the type of the measuring cell and the intended use, and is located in the electrolyte space. These electrolytes, e.g., phosphoric acid or sulfuric acid, possess more or less corrosive properties. It is therefore necessary to hermetically seal the electrolyte space, because injuries can otherwise occur and measuring or evaluating devices may be damaged during the handling of the measuring cell. The electrolyte space is sealed by O-rings, bonding and/or welding according to the state of the art.

It was now found that these measures are not sufficient, because the electrolyte can escape at the connection point between the housing wall and the measuring cell cover or even along the contact wires, which usually consist of platinum. These leaks occur especially in the case of great variations in temperature, because the materials to be combined (precious metals, plastics) have greatly different coefficients of thermal expansion.

SUMMARY AND OBJECTS OF THE INVENTION

The basic object of the present invention is to improve an electrochemical measuring cell such that hermetic sealing is possible in a housing of a slightly modified design to prevent electrolytes from escaping.

This object is accomplished by providing a recess extending in parallel to the circumferential direction of the housing wall between the measuring cell cover and the housing, which recess is filled with an electrolyte- and temperature-resistant sealing material.

The advantage of the present invention is that prior-art materials can be used as the sealing material, and that only simple design changes are necessary. A chemical-resistant resin, grease or silicone adhesive is used as the sealing material. Suitable materials are, e.g., epoxy resins without curing agent, silicone-based high-vacuum grease, or high-vacuum grease based on polytetrafluoroethylene.

It proved to be especially advantageous to inject the sealing material through a small opening into the recess extending in parallel to the housing wall. It is also advantageous to lead the contact wires through the recess and to embed them in the sealing material.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

BRIEF DESCRIPTION OF THE DRAWINGS

In the drawings:

The only FIGURE is a schematic longitudinal sectional view of an electrochemical measuring cell according to the invention.

DESCRIPTION OF THE PREFERRED EMBODIMENT

The only FIGURE shows a schematic detail of a longitudinal section of one side of the housing of an electrochemical measuring cell with a housing 1, which is cylindrical in this embodiment and is definitely impermeable to the electrolyte, although permeable to gases in this case. A suitable material is, e.g., polytetrafluoroethylene (PTFE). The detail represented shows the counterelectrode 2, which is connected to a contact wire 4 on its underside. The electrolyte space and the other components of the electrochemical measuring cell, not shown, are located within the housing 1 under the counterelectrode 2.

An essential part of the present invention is the recess designed as a groove-like annular space 6, which is formed in the simplest case by the inner wall of the housing 1 being shortened by the height of the annular space 6, while the dimensions of the other components of the measuring cell are the same. The contact wires 4 of the measuring cell are led diagonally through the annular space 6 in the right-hand part of the figure, and then they are led out between the outer wall of the housing 1 and the measuring cell cover 3 to a conductor board with electronic signal-amplifying and optionally other suitable signal-processing elements and finally to a connector 5 for transmitting the signals for the further evaluation or display. In the simplest case, the annular space 6 is filled with a suitable sealing material through at least one opening 7 after the mounting of the measuring cell. The opening 7 may be designed as a hole in the measuring cell cover 3. The task of the sealing material is to prevent leakage of the electrolyte even in the case of great variations in temperature and pressure shocks and to hermetically embed the contact wires 4. Chemical-resistant resins, greases or adhesives proved to be suitable materials. Epoxy resins without curing agent are used in the exemplary embodiment. Silicone-based, high-vacuum greases are also suitable sealing materials, as are silicone adhesives.

While a specific embodiment of the invention has been shown and described in detail to illustrate the application of the principles of the invention, it will be understood that the invention may be embodied otherwise without departing from such principles.

What is claimed is:

1. An electrochemical measuring cell for detecting components in fluid media, comprising:

a housing accommodating a counterelectrode, a measuring electrode and an electrolyte, said counterelectrode and measuring electrode being in liquid connection with said electrolyte;

a gas-permeable, electrolyte impermeable diaphragm disposed on one side of said housing, said diaphragm for allowing diffusion contact with said measuring electrode from one side of said housing;

a measuring cell cover disposed on another side of said housing, said housing being closed by said measuring cell cover, said housing having a recess formed on an inner side of said housing extending in parallel to a circumferential direction of said housing, said recess and an inside surface of said cover cooperating to define a space between said measuring cell cover and said housing; and electrolyte-temperature-resistant sealing material means filling said space.

2. An electrochemical measuring cell according to claim 1, further comprising contact wires led through said electrolyte- and temperature-resistant sealing material means filling said space.

3. An electrochemical measuring cell according to claim 2, wherein said contact wires extend obliquely from an inside of said cell to an outside of said cell through said recess and are imbedded in said sealing material means, and said space is an annular space.

4. An electrochemical measuring cell according to claim 1, wherein said sealing material means is an epoxy resin without curing agent.

5. An electrochemical measuring cell according to claim 1, wherein said sealing material means is a high vacuum grease based on silicone.

6. An electrochemical measuring cell according to claim 1, wherein said sealing material means is polytetrafluoroethylene grease.

7. An electrochemical measuring cell according to claim 1, wherein said sealing material is a silicone adhesive.

8. An electrochemical measuring cell according to claim 1, wherein said sealing material means is selected from the group consisting of epoxy resin without curing agent, a high vacuum grease based on silicone, a high vacuum grease based on polytetrafluoroethylene, and a silicone adhesive.

9. An electrochemical measuring cell according to claim 1, further comprising an opening through one of said cell covering and said housing, said opening leading into said recess of said housing.

10. An electrochemical measuring cell for detecting components in fluid media, comprising:

a housing accommodating a counterelectrode, a measuring electrode and an electrolyte, said counterelectrode and measuring electrode being in liquid connection with said electrolyte;

gas-permeable electrolyte impermeable means forming a part of said housing for allowing diffusion contact with said measuring electrode;

a measuring cell cover disposed on a side of said housing, said housing being closed by said measuring cell cover, said housing and said measuring cell cover cooperating to define an annular space extending substantially in parallel to a circumferential direction of said housing between said measuring cell cover and said housing; and electrolyte-temperature-resistant sealing material means filling said annular space.

11. An electrochemical measuring cell according to claim 10, further comprising contact wires led through said electrolyte- and temperature-resistant sealing material means filling said annular space, said contact wires extending obliquely from an inside of said cell to an outside of said cell through said recess and being imbedded in said sealing material means.

12. An electrochemical measuring cell according to claim 10, wherein said sealing material means is an epoxy resin without curing agent.

13. An electrochemical measuring cell according to claim 10, wherein said sealing material means is a high vacuum grease based on silicone.

14. An electrochemical measuring cell according to claim 10, wherein said sealing material means is polytetrafluoroethylene grease.

15. An electrochemical measuring cell according to claim 10, wherein said sealing material is a silicone adhesive.

16. An electrochemical measuring cell according to claim 10, wherein said sealing material means is selected from the group consisting of epoxy resin without curing agent, a high vacuum grease based on silicone, a high vacuum grease based on polytetrafluoroethylene, and a silicone adhesive.

17. An electrochemical measuring cell according to claim 10, further comprising an opening through one of said cell covering said housing leading into said recess.

18. An electrochemical measuring cell for detecting components in fluid media, comprising:

a housing accommodating a counterelectrode, a measuring electrode and an electrolyte, said counterelectrode and measuring electrode being in liquid connection with said electrolyte;

gas-permeable electrolyte impermeable means forming a part of said housing for allowing diffusion contact with said measuring electrode;

a measuring cell cover disposed on another side of said housing, said housing being closed by said measuring cell cover, said housing having a recess formed on an inner side of said housing extending in parallel to a circumferential direction of said housing, said recess and an inside surface of said cover cooperating to define a space between said measuring cell cover and said housing; and electrolyte-temperature-resistant sealing material means filling said space.

19. An electrochemical measuring cell according to claim 18, further comprising contact wires led through said electrolyte- and temperature-resistant sealing material means filling said space.

20. An electrochemical measuring cell according to claim 18, wherein said sealing material means is selected from the group consisting of epoxy resin without curing agent, a high vacuum grease based on silicone, a high vacuum grease based on polytetrafluoroethylene, and a silicone adhesive.

* * * * *